United States Patent [19]

Tamaoku et al.

[11] 4,201,548

[45] May 6, 1980

[54] METHOD FOR DETERMINING VOLATILE SUBSTANCES IN AN AQUEOUS SOLUTION AND APPARATUS THEREFOR

[75] Inventors: Katsuki Tamaoku; Keishi Nakahara; Hideo Sumiyoshi; Masahiro Tachibana, all of Kumamoto, Japan

[73] Assignee: Dojindo Laboratory & Co., Ltd., Kamamoto, Japan

[21] Appl. No.: 871,580

[22] Filed: Jan. 23, 1978

[30] Foreign Application Priority Data

Jan. 25, 1977 [JP] Japan .................................. 52-6389

[51] Int. Cl.² ...................... G01N 33/00; G01N 33/16
[52] U.S. Cl. .................. 23/230 R; 23/230 B; 23/230 M; 422/56; 422/57; 422/58; 422/68; 422/87
[58] Field of Search ... 23/230 B, 230 M, 230 R (U.S. only), 23/253 R, 253 TP, 254 R (U.S. only); 73/19; 422/55, 56, 57, 58, 68, 83, 86, 87, 88

[56] References Cited

U.S. PATENT DOCUMENTS

| 3,000,706 | 9/1961 | Royce .......................... 23/254 R X |
| 3,404,962 | 10/1968 | Medlar et al. ..................... 23/253 R |
| 3,420,635 | 1/1969 | Davis ............................... 23/253 TP |
| 3,545,931 | 12/1970 | McKinley, Jr. ............... 23/254 R X |
| 3,791,933 | 2/1974 | Moyer et al. ................. 23/253 TP X |
| 3,866,460 | 2/1975 | Pearce, Jr. ..................... 23/253 R X |
| 3,913,393 | 10/1975 | Facy ................................ 23/230 R X |
| 3,992,153 | 11/1976 | Ferber et al. ................. 23/253 TP X |

*Primary Examiner*—Joseph Scovronek
*Attorney, Agent, or Firm*—Frank J. Jordan

[57] ABSTRACT

A method for detecting and determining a volatile or volatilizable substance in an aqueous solution or liquid and an apparatus employed for this method are disclosed. The volatile component, vaporized from the solution through a water repellent and gas permeable membrane, is brought into contact with a dried or partially dried transparent film-like color developing carrier which is provided adjacent to the membrane, and the determination is carried out by the degree of color-change of the carrier. The apparatus comprises a cover plate with sample holes, a membrane, a color developing carrier, and a cover plate with observation windows. The members are fitted tightly together to form a single composite layer.

10 Claims, 4 Drawing Figures

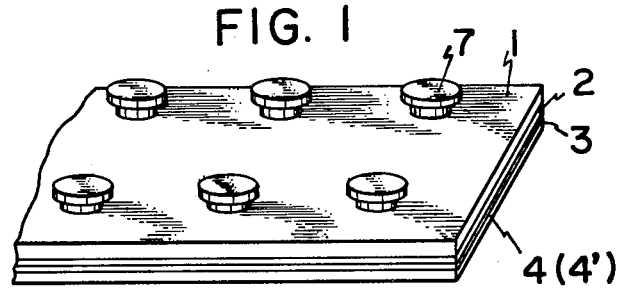
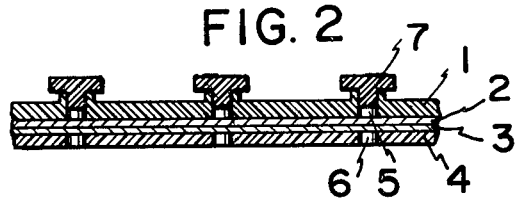
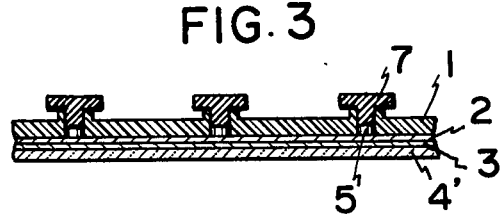
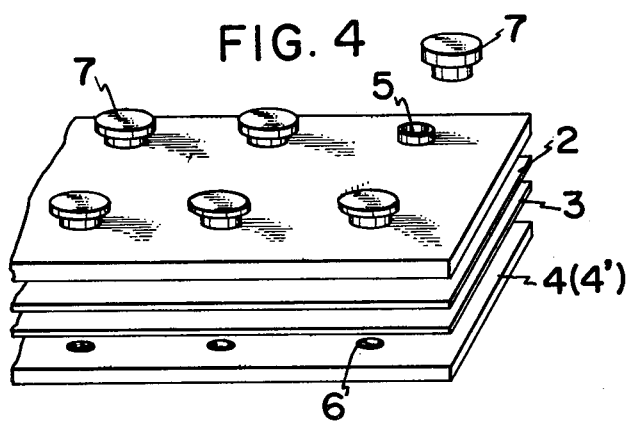

METHOD FOR DETERMINING VOLATILE SUBSTANCES IN AN AQUEOUS SOLUTION AND APPARATUS THEREFOR

BACKGROUND OF THE INVENTION

1. Field of the Invention

This invention relates to the method and the apparatus for detecting and determining volatile or volatilizable substances, simply and rapidly, in aqueous solutions or liquids, such as ammonia (including ammonium salts), volatile amines (including amine salts), halogens, nitrogen oxides and sulfur compounds. The volatile amines which can be determined according to the present invention include monomethyl amine, mono-ethyl amine, dimethyl amine, diethyl amine, trimethyl amine and triethyl amine.

2. Description of the Prior Art

At present, the prevalent colorimetric methods for determining ammonia in blood in clinical tests, such as Nessler's or the Indophenol methods, have defects in that: (1) a large amount of sample (1 to several mls.) is required; (2) a calibration curve has to be drawn for each determination; (3) a longer period of analysis (2 to 3 hours) is required; (4) the procedure is troublesome; (5) temperature influences the results seriously; and (6) poisonous and deleterious reagents have to be used. In spite of the above mentioned defects, these methods have been used long years in practical use.

SUMMARY OF THE INVENTION

An object of the invention is to provide a method for detecting and determining simply, quickly and accurately a volatile or volatilizable substance in an aqueous solution, in which all of these defects are overcome.

A further object of the invention is to provide an apparatus which is suitable for carrying out the above mentioned detecting and determination of the volatile or volatilizable substance.

In short, a feature of this invention is the provision of a simple and quick method for detecting and determining a volatile or volatilizable substance in an aqueous solution or liquid. This comprises supplying a sample into a sample hole which provides a water repellent, liquid tight and gas permeable membrane 2 produced from polymers such as polytetrafluoroethylene, polypropylene and the like in which a vaporizing agent can be charged previously or without charging it and then closing the hole 5 immediately, and separating gas of the volatile or volatilizable substance contained in the sample through the membrane 2. The gas then comes in contact with a dried or partially dried film-like or thin layer-like color developing carrier 3 with high transparency which is arranged in contact with the membrane 2 and coated or impregnated with an indicator and results in the development of a color change on the carrier 3. The detection and determination of the volatile or volatilizable substance is carried out through comparison of the degree of color change with a standard.

In a preferred embodiment in accordance with the invention the volatile or volatilizable substance is selected from the group consisting of ammonia and sulfur compounds.

Further, in another preferred embodiment in accordance with the invention, the color developing carrier 3 is selected from the group consisting of a combination of dextran beads or a substance which has similar chemical and physical properties thereto and a polyethylene adhesive tape, membrane filters produced from cellulose acetate, polypropylene resin, cellophane film and the like.

Moreover, in accordance with the invention, an apparatus for the rapid determination of a volatile or volatilizable substance in an aqueous solution or liquid in a closed system comprises a cover plate 1 having sample holes 5 and stoppers or covers 7 which provide spaces in the holes 5 when the holes are closed with the stoppers or covers, a membrane 2 which is water repellent, liquid tight and gas permeable, a dried or partially dried film-like or thin layer-like color developing carrier 3 with high transparency and coated or impregnated with an indicator which changes color by contact with a volatile component, and a cover plate 4 having observing windows 6 matching individually with the sample holes, or a transparent cover plate 4' having no observing windows, the foregoing members being fitted tightly in order to form a single composite layer.

Still further, in another preferred embodiment in accordance with the invention, the sample hole 5 is charged with solid alkali or solid acid or a carrier impregnated with an alkaline or acid solution which serves as a vaporizing agent to form a vaporizing component.

In this invention, the polymers such as polytetrafluoroethylene resin and polypropylene and the like are used as the material for the water-repellent, liquid light and gas permeable membrane. As the color developing carrier, a relatively highly transparent and porous gas permeable film, for example, membrane filter such as cellophane film impregnated with a chromogenic reagent which changes color by a volatile substance and thereafter dries, or an adhesive tape on which hydrophilic gel-like micro beads coated or impregnated with the chromogenic reagent are spread in a thin layer, are suitably used.

The porous gas permeable membrane which is suitable to use in the present invention is produced from the one selected from the group consisting of polyethylene, polypropylene and polytetrafluoroethylene.

The membrane filter which is suitable in the invention is produced from the one selected from the group consisting of cellulose nitrate, cellulose acetate, polyvinyl chloride, polyamine and polytetrafluoroethylene.

The list of the chromogenic agents which are usable in the invention is as follows:
Phenol Red
Neutral Red
3,4,5,6-tetrabromophenol sulfonphthalein
Brilliant Yellow
Bromothymol Blue
Bromophenol Red
Bromocresol Purple
Chlorphenol Red
Ethyl Red
Alizarin Red
Methol Red
Ethyl Orange
Bromochlor Blue
Methyl Orange
Congo Red
Chlorphenol Blue
Bromophenol Blue
para-nitrosphenol
Xylenol Orange
Bromocresol Green
Nessler's Reagent cupric Sulfate Because the color developing carrier is porous and gas permeable, the gaseous volatile substance passes through said carrier easily and reacts with the chromogenic agent which is coated or impregnated onto said carrier and develops color in a short time.

BRIEF DESCRIPTION OF THE DRAWINGS

The invention is described in detail hereinafter in connection with the drawings in which:

FIG. 1 is a perspective view of an apparatus according to the invention;

FIG. 2 and FIG. 3 are cross sections taken along line A—A of FIG. 1; and

FIG. 4 is a perspective view of the apparatus of FIG. 1 before assembling.

DESCRIPTION OF THE PREFERRED EMBODIMENTS

In FIGS. 1 to 4, the numeral 1 designates a plastic cover plate of about 3 mm thickness in which a plurality of sample holes 5 are opened for the introduction of the sample solution. Numeral 7 designates a stopper or a cover for the sample hole 5. Numeral 2 designates a hydrophobic, gas permeable membrane. Numeral 3 designates a transparent film-like color developing carrier coated or impregnated with chromogenic reagent that changes color by a volatile component which passes through the membrane 2. Numeral 4 is a plastic cover board which has observation windows 6 corresponding to the positions of the sample holes 5. Numeral 4' designates a transparent cover plate having an identical construction without observation windows. Further, these parts are fitted together to form a single composite layer.

Instead of the stopper, an inactive and gas tight film such as aluminum foil coated with an adhesive material which enables the foil to adhere to the plastic cover plate may be used.

In an actual measurement, a sample is poured into the sample hole 5, and a specific vaporizing agent is added therewith; the hole is closed immediately with a stopper. As the vaporizing agents for ammonia and amines, non-volatile alkali agents are used, and for halogens, sulfur compounds and nitrogen oxides, non-volatile acid agents are employed. The component vaporized by means of the vaporizing agent is released and permeated through the membrane 2. Water and non-volatile vaporizing agents remain in the sample hole without permeating through the membrane because of the characteristic hydrophobic property and water-tight properties of the membrane. In this way, only the vaporizing component comes in contact with the chromogenic reagent contained in the color developing carrier 3. By observing the degree of color change of the chromogenic reagent through the observation windows 6 on the cover plate 4, the degree of evolution of the volatile component, that is, the concentration of volatile substance in the sample can be determined. If the cover plate 4' is made of a transparent sheet, the observation windows 6 are not required.

By using the above mentioned apparatus, the members fitted tightly to one another, a number of measurements can be performed simultaneously without the problem of the specimen in one sample hole mixing or influencing the other specimens in the neighboring sample holes.

One of the characteristics of this invention is that the chromogenic reagents contained in the color developing carrier are in the form of a dried or partially dried thin layer or film, which contains 0 to 30% by weight of water.

In the case of the thin layer, it is desirable that either the chromogenic reagent or beads impregnated with the chromogenic reagent be adhered to a transparent tape in the form of a thin layer. Because of this, even very small quantities of gaseous material which permeate through the membrane can be determined, as the chromogenic reagents according to the present invention show very much higher sensitivity than when used in a solution form. When the determining apparatus of this invention is used, the amount of specimen to be tested is generally 25-30 $\mu$l. This is very advantageous in biochemical and clinical analyses where very limited samples are available. For instance, in the case of determination of ammonia in blood, the fact that the determination can be carried out with such limited quantities as 25-30 $\mu$l means that this method is applicable in cases involving new-born babies and other cases where removal of blood can be serious. The determination of ammonia in blood of new-born babies is considered to be an urgent and paramount matter in order to prevent the occurrence of abnormal children, but the amount of blood that can be taken from them is usually limited to the smallest quantity obtainable. Thus, with the conventional method, the determination is difficult and also consumes much time. A very small quantity of ammonia permeated through the membrane of this invention does not produce any change of color with an aqueous solution of a conventional pH indicator dye which is used in the alkaline range. On the other hand, when the developing carrier 3 is impregnated with the same aqueous solution of the pH indicator and then well dried, as in the determining apparatus of this invention, a distinct change of color is observed even with traces of ammonia. Therefore, by forming the developing carrier 3 into a solid and transparent thin film as described above, a definite improvement in the sensitivity for traces of ammonia is evident when compared with that obtainable with a solution form. The apparatus of this invention has also an additional merit in that the observation of the change of color can be done directly by providing the observation windows 6.

The following can be suitably used as the color-developing carrier 3 which produces the advantages according to the present invention.

(1) The thin film which is prepared by spreading the hydrophilic gel beads (for instance, beads of agar, cross-linked dextran, or cellulose derivatives, having about 150 to 200 mesh size), which are coated or impregnated with the chromogenic reagent and then well-dried, on the transparent adhesive tape in a thin or single layer.

(2) A relatively transparent, porous and gas permeable thin membrane, such as membrane filters or cellophane film, which is coated or impregnated with the chromogenic reagent and well-dried.

The apparatus of this invention requires only a short time, such as 5 to 8 minutes, in determining the ammonia content in blood, with the operation being so simple that even a non-professional can use it without difficulty. Moreover, as this apparatus is not influenced by the ambient conditions such as temperature and reaction time, it has many advantages as a quick analytical device for clinical tests and bio-chemical measurements and as a portable determination apparatus for various substances in factories. This apparatus can be used more conveniently by placing a small amount of solid acid or alkali, or a piece of carrier such as filter paper, glass fibre, or other inactive porous compounds, impregnated with a solution of acid or alkali, in the sample hole 5 in advance. The measurement may then be carried out instantaneously by simply inserting a specimen into the sample hole.

In the conventional test and measurement, the amount of alkali or acid added may greatly influence the results to be obtained; therefore, it is usually necessary to accurately control the amounts of these reagents. It takes time and is troublesome to prepare and adjust these reagent solutions. However with the apparatus of this invention, once certain amounts of alkali or acid in a solid form are prepared or impregnated into the carrier, such as filter paper, and put into the sample hole 5 in advance, control of the amount of the alkali or acid is unnecessary. This saves performance time and simplifies the determination process and indeed decreases any measuring error between testers. This apparatus is also portable and convenient for carrying about.

The method of this invention will be further described with reference to the following specific examples.

EXAMPLE 1

A micro-porous thin film of polytetrafluoroethylene resin (a product of Junkosha Co., Ltd. of Japan, Gore Tex ®, the thickness 0.19 mm, the maximum pore diameter $3\mu$), was used as the membrane. The color-developing carrier was prepared by spreading the cross-linked dextran beads (a product of Pharmacia Fine Chemicals, Sephadex ® G-15, 40–120$\mu$), which were impregnated with 0.3% bromocresol green aqueous solution in a ratio of 1 ml/g (dry weight) and well dried, on a colorless, transparent and adhesive polyethylene tape (about 0.1 mm thick, about 10 mm width) to form a single layer. Both the membrane and the carrier were placed in the described apparatus.

As a sample for testing, 25 $\mu$l of human blood, urine or waste water was poured into the sample hole 5. Then, 25 $\mu$l of potassium carbonate saturated aqueous solution was immediately added to the sample hole and then stoppered. After about 5 to 8 minutes, the degree of the color change of the developing carrier was observed through the observation window on the cover plate, and the color intensity was compared with a standard color chart prepared previously using standard solutions.

By this method, 0 to 50 ppm of ammonia can be determined simply and quickly by using a micro quantity of the sample for testing, with very little deviations in results obtained by different operators or when compared with conventional methods. Preferably, the range of the ammonia which can be determined is from 0.5 to 10 ppm. Thus, it was ascertained that the method according to the invention has a high degree of utility as well as effectiveness.

The following table is one exemplification comparing the results between the conventional Indophenol method and the present method.

| Methods of Determination | The Method of this Invention | | | (Unit: ppm) Indophenol Method | | |
|---|---|---|---|---|---|---|
| Operators | A | B | C | A | B | C |
| Samples 1. human blood | 0–1 | 0–1 | 0–1 | 0.50 | 0.67 | 0.52 |
| 2. human blood | 1–2 | 1–1.5 | 1–2 | 1.53 | 1.40 | 1.73 |
| 3. urine | 2 | 2 | 2–2.5 | 2.01 | 2.05 | 2.24 |
| 4. waste water | 3 | 3–4 | 3 | 3.11 | 2.96 | 3.40 |
| 5. waste water | 4–5 | 4–5 | 4–5 | 4.45 | 4.82 | 5.12 |

EXAMPLE 2

This example was carried out in the same manner as Example 1, except that, instead of potassium carbonate saturated aqueous solution, either 10 mg of mixed powder in the ratio of 5:1 (weight ratio) of potassium carbonate and sodium carbonate or a piece of thick filter paper impregnated with the equivalent quantity of this mixed powder was placed into the sample holes in advance. At the time of actual determination, 25 $\mu$l of sample was inserted into the sample hole and the determination was carried out in the same way as in Example 1. After about 5 to 8 minutes, the color change of the developing carrier was observed through the observation window of the cover plate, and the color intensity was compared with a standard color chart. The result of the determination was nearly the same as that obtained in Example 1. Moreover, it was proved that this modification, in which the solid alkaline substance was placed in the sample holes in advance, increased the detection sensitivity one and a half or twofold over the method described in Example 1 and also enhanced the simplicity and quickness of the operation.

EXAMPLE 3

This example was carried out in the same manner as Example 2, except that, instead of the color developing carrier as described in Example 1, a cellulosic membrane filter (a membrane filter manufactured by Sartorius, 0.15 mm of thickness, 0.8$\mu$ of average pore diameter), which was impregnated with 0.06% bromocresol green aqueous solution at the ratio 5 ml/100 cm$^2$ and dried, was used. The result was almost the same as that of Example 2. However, in this example a longer reaction time was required for full color change as compared with that required in Example 2. This is considered to be due to the differences of the density and transparency of the material comprising the color developing carrier.

EXAMPLE 4

By using a microporous polytetrafluoroethylene sheet (Polyflonpaper by Daikin Industry Co., 0.55 mm thick, 45$\mu$ maximum pore diameter; or Fluoropore by Sumitomo Electric Ind., 0.05 mm thick and 1.0$\mu$ average pore diameter), or microporous polypropyrene resin (Duraguard by Polyplastics Inc., 0.25 mm thick, 0.016$\mu$ average pore diameter) as the membrane, and by using a mono layer sheet of cross-linked dextran beads (as indicated in the operation of Example 1) impregnated with bromphenol blue, bromothymol blue or methyl red instead of bromcresol green, as a color developing carrier, the operation was conducted in just the same manner as in Example 2. As a result with regard to all of the membranes used, there was no noticeable difference. With relation to the chromogenic reagents, bromcresol green was most suitable in its color tone and sensitivity.

EXAMPLE 5

A color developing carrier was prepared in a similar manner as in Example 1 by spreading the dried cross-linked dextran beads, which had been impregnated with 0.05% fluorescein aqueous solution at the ratio of 1 ml/g (dry weight), on the colorless and transparent adhesive polyethylene tape (about 0.1 mm thick, about 10 mm width). The apparatus with this color developing carrier was used for the determination of inorganic bromides. As the porous membrane, the commercially available porous tetrafluoroethylene resin film was used same as in Example 1.

Twenty five μl of an aqueous sample solution containing potassium bromide was put into a sample hole by means of a micro pipette. Then, 25 μl of 10% potassium chromate aqueous solution and 25 μl of 1% sulfuric acid aqueous solution were added to the hole immediately. About 5 minutes later, the degree of color-change on the color developing carrier by bromine which is formed by said oxidizing agent was observed through the observation window, and then compared with the prepared standard color chart to determine the concentration of bromide in the sample. With this method, bromine contained in the bromide sample could be determined in the range from 0.1 to 10 ppm.

The following table shows a comparison of the results obtained by the present method and the already known sodium thiosulfate titration method. From the table, it can easily be understood that the method of the present invention requires only a very small quantity of sample and has a relatively high accuracy in measurement. The deviation of the data among the different operators is reasonably small, even though the present method is a simple and rapid method requiring a very small quantity of sample.

| Method of Determination | | Method of This invention*1 | | | (unit: ppm) Thiosulfate Titration*2 Method | | |
|---|---|---|---|---|---|---|---|
| Operators | | A | B | C | A | B | C |
| Samples | 1. 0.45 | 0–0.5 | 0–0.5 | 0–0.5 | 0.47 | 0.56 | 0.35 |
| (Prepared | 2. 1.55 | 1–1.5 | 1.5–2 | 1.5–2 | 1.82 | 1.45 | 1.66 |
| Values) | 3. 3.85 | 3–4 | 3–4 | = 4 | 3.82 | 4.25 | 4.00 |
| | 4. 5.50 | 5–6 | 5–6 | = 6 | 5.10 | 5.35 | 5.90 |
| | 5. 7.80 | = 8 | 7–8 | = 8 | 8.00 | 7.51 | 8.20 |

Note
*1The amount of the sample is 25 μl
*2The amount of sample is 10–50ml

EXAMPLE 6

As the chromogenic reagent, 1% cupric nitrate aqueous solution was used to impregnate cross-linked dextran beads in a ratio of 1 ml/g (dry weight). The color developing carrier was prepared in a similar manner as described in the previous Example 5. This preparation can be used for the determination of inorganic sulfide compounds.

As the porous membrane, the commercially available polytetrafluoroethylene resin film same as Example 1 was used. Twenty-five μl of sample solution containing sulfur compounds (metallic sulfides such as iron sulfide, copper sulfide or sodium sulfide) was put into the sample hole, then 23 μl of 1% sulfuric acid was added, and the sample hole was stoppered immediately. About 5 to 10 minutes later, the degree of color-change by sulfur dioxide which is formed by the sulfuric acid on the color developing carrier was observed through the observation window, and then compared with the standard color chart to determine the concentration of sulfur in the sample.

By this method, sulfur contained from 0.1 to 10 ppm in the samples could be determined.

The following table shows a comparison of the results obtained from the present method and the already known sodium thiosulfate titration method. As can be seen, the determination by this method is accurate enough even though this is a rapid and simple method based on a very small quantity of sample.

| Method of Determination | | Method of this Invention | | | (Unit: ppm) Thiosulfate Titration Method | | |
|---|---|---|---|---|---|---|---|
| Operators | | A | B | C | A | B | C |
| Samples (prepared values) | sodium sulfide 1.00 | 0–1 | 0.5–1 | 0.5–1 | 1.00 | 0.98 | 1.10 |
| | sodium sulfide 1.55 | 1–2 | 1.5–2 | 1.5–2 | 1.35 | 1.58 | 1.68 |
| | copper sulfide 3.85 | 3–4 | 3–4 | 3.5–4 | 3.31 | 3.58 | 3.82 |
| | copper sulfide 5.50 | 5–6 | = 6 | 5–6 | 5.35 | 5.00 | 5.80 |
| | iron sulfide 9.00 | 8–10 | = 9 | 8–10 | 8.80 | 9.50 | 9.40 |

EXAMPLE 7

A microporous thin film of polypropylene resin (the product of Polyplastics Co., Ltd. of Japan, Duraguard, 0.025 mm thickness, 0.016μ average pore diameter) was used as the membrane. The color-developing carrier was prepared by depositing the cross-linked dextran beads, which were impregnated with 0.3% bromcresol green aqueous solution in a ratio of 1 ml/g (dry weight) and partially dried to the extent of 15 to 20% of water content, on a colorless, transparent and adhesive polyethylene tape (0.1 mm thickness, 10 mm width) to form a single layer. The determination was carried out according to the method of Example 1 using the same samples as Examples, and the result was compared with that of Example 1 which used the dry beads.

Generally, for the sample which contains relatively low concentration of an objective component, the color-developing sensitivity obtained by use of the partially dried beads was found to decrease somewhat compared with that which was obtained by use of the dry beads. On the other hand, for the sample which contains relatively high concentration of the objective component, the half dried beads showed good evenness of color.

When this method is applied to the determination of ammonia in blood, it has the following merits: (1) the required amount of sample can be as small as 25–30 μl; (2) there is no need of preparing a calibration curve for each determination because the coloration is compared with the standard color chart; (3) required time for each determination is very short (5 to 8 minutes); (4) the analytical procedure is quite simple; (5) the method is unaffected by temperature; and (6) poisonous and deleterious reagents need not be used.

What we claim is:

1. A rapid method for detecting and determining a volatile or a volatizable substance in a sample aqueous solution or liquid comprising the steps of:

coating or impregnating a transparent film carrier with a chromogenic reagent to form a transparent color developing film-like element;

contacting said color developing film-like element with a gas permeable membrane which is hydrophobic;

placing a sample within a sample hole in which a part of the sample hole is defined by a part of said gas permeable membrane;

closing the sample hole from the surrounding atmosphere;

separating the volatile component of the sample by passing the volatile component through the gas permeable membrane;

contacting said separated volatile component with said color developing film-like element; and detecting and determining the volatile or volatizable substance by the degree of color change of the chromogenic reagent.

2. The method according to claim 1 comprising placing a vaporizing agent in said sample hole prior to placing said sample therein to release the volatile component, said vaporizing agent being used when a volatizable substance is dissolved in the sample.

3. The method according to claim 2 wherein said vaporizing agent is solid alkali or solid acid or a carrier impregnated with an alkaline or acid solution.

4. The method according to claim 1 wherein said step of closing the sample hole comprises inserting a stopper in the sample hole.

5. The method according to claim 1, wherein the volatile substance is selected from the group consisting of ammonia and sulfur compounds.

6. The method according to claim 1 wherein said color developing film-like element comprises hydrophilic gel beads coated with the chromogenic reagent and coated or impregnated on the transparent film carrier.

7. The method according to claim 6 wherein said hydrophilic gel beads are selected from the group consisting of dextran, agar and cellulose derivatives.

8. The method according to claim 1 wherein said transparent film carrier is selected from the group consisting of polyethylene tape and membrane filters produced from cellulose acetate, polypropylene resin, and cellophane film.

9. The method according to claim 1 wherein said gas permeable membrane is selected from the group consisting of polyethylene, polypropylene, and polytetrafluoroethylene.

10. An apparatus for the rapid determination of a volatile or a volatizable substance in a sample aqueous solution or liquid comprising a first cover element having a plurality of holes for receiving the sample, closing means for closing off said sample holes from the surrounding atmosphere, a gas permeable membrane contacting said first cover element and defining a portion of said sample holes, said gas permeable membrane being hydrophobic, a dried or partially dried transparent film-like color developing carrier coated or impregnated with an indicator which changes color by contact with the volatile component of the sample, said film-like color developing carrier being in contact with said gas permeable membrane, and a second cover element contacting said film-like color developing carrier, said second cover element being constructed and arranged to permit viewing of at least parts of said film-like color developing carrier which are aligned with said sample holes, said first cover element, gas permeable membrane, film-like color developing carrier, and second cover element being fitted together to form a single composite layer, said sample holes receiving a sample whereby the volatile component of the sample is separated by passing through the gas permeable membrane to contact the film-like color developing carrier such that the volatile or volatizable substance is detected and determined by the degree of color change of the film-like color developing carrier.

* * * * *